(12) United States Patent
Sasaki et al.

(10) Patent No.: US 10,646,841 B2
(45) Date of Patent: May 12, 2020

(54) BONE CEMENT MIXING AND DELIVERY SYSTEM WITH REDUCED FUME EXPOSURE

(71) Applicant: Medtronic Holding Company Sàrl, Tolochenaz (CH)

(72) Inventors: Neil S. Sasaki, Santa Clara, CA (US); Bryan A. Click, Fremont, CA (US)

(73) Assignee: MEDTRONIC HOLDING COMPANY SARL, Tolochenaz (CH)

( * ) Notice: Subject to any disclaimer, the term of this patent is extended or adjusted under 35 U.S.C. 154(b) by 713 days.

(21) Appl. No.: 15/218,885

(22) Filed: Jul. 25, 2016

(65) Prior Publication Data

US 2016/0332130 A1     Nov. 17, 2016

Related U.S. Application Data

(63) Continuation of application No. 13/735,608, filed on Jan. 7, 2013, now Pat. No. 9,480,955.

(51) Int. Cl.
*B01F 15/02*     (2006.01)
*A61B 17/88*     (2006.01)
*B01F 15/00*     (2006.01)

(52) U.S. Cl.
CPC ...... *B01F 15/0212* (2013.01); *A61B 17/8833* (2013.01); *B01F 15/00993* (2013.01); *B01F 15/0206* (2013.01); *B01F 15/0237* (2013.01); *B01F 15/0258* (2013.01); *A61B 2017/8838* (2013.01); *B01F 2215/0029* (2013.01)

(58) Field of Classification Search
CPC ............. B01F 15/0206; B01F 15/0212; A61B 17/8833

USPC ..... 366/130, 139, 189; 206/222; 604/82, 87, 604/88
See application file for complete search history.

(56) References Cited

U.S. PATENT DOCUMENTS

| | | | |
|---|---|---|---|
| 3,595,439 A | 7/1971 | Newby et al. | |
| 4,676,655 A | 6/1987 | Handler | |
| 5,067,948 A * | 11/1991 | Haber | A61M 5/2448 604/192 |
| 5,393,497 A * | 2/1995 | Haber | A61J 1/2089 137/68.11 |
| 5,435,645 A | 7/1995 | Faccioli et al. | |
| 6,024,480 A | 2/2000 | Seaton et al. | |
| 6,296,149 B1 | 10/2001 | Long | |
| 6,592,251 B2 | 7/2003 | Edwards et al. | |
| 6,921,192 B2 | 7/2005 | Vendrely et al. | |
| 7,018,089 B2 | 3/2006 | Wenz et al. | |
| 7,547,293 B2 * | 6/2009 | Williamson | A61M 5/30 604/70 |
| 7,841,763 B2 | 11/2010 | Foster et al. | |

(Continued)

*Primary Examiner* — Charles Cooley
(74) *Attorney, Agent, or Firm* — Sorell, Lenna & Schmidt, LLP

(57) ABSTRACT

A system for bone cement includes a vial holder configured for receiving a vial and including a holding structure for maintaining the vial in the vial holder. The vial includes a monomer component for bone cement. A holder chamber is configured to receive and secure the vial holder. The vial holder is advanced toward a vial-breaking device for breaking the vial and releasing its contents into the holder chamber past the elastomeric seal. Once the vial holder is advanced further the elastomeric seal is deformed to form a seal and prevent fumes produced from escaping from the device.

19 Claims, 3 Drawing Sheets

(56) References Cited

U.S. PATENT DOCUMENTS

| | | | |
|---|---|---|---|
| 8,038,682 B2 | 10/2011 | McGill et al. | |
| 8,132,959 B2 * | 3/2012 | Smit | A61B 17/8833 |
| | | | 206/222 |
| 9,480,955 B2 * | 11/2016 | Sasaki | B01F 15/0206 |
| 2008/0037362 A1 * | 2/2008 | Axelsson | B01F 13/06 |
| | | | 366/139 |
| 2013/0269826 A1 * | 10/2013 | Sasaki | A61B 17/8827 |
| | | | 141/2 |
| 2014/0192611 A1 * | 7/2014 | Sasaki | B01F 15/0206 |
| | | | 366/139 |
| 2016/0332130 A1 * | 11/2016 | Sasaki | B01F 15/0206 |
| 2019/0183552 A1 * | 6/2019 | Kluge | B01F 15/0206 |

* cited by examiner

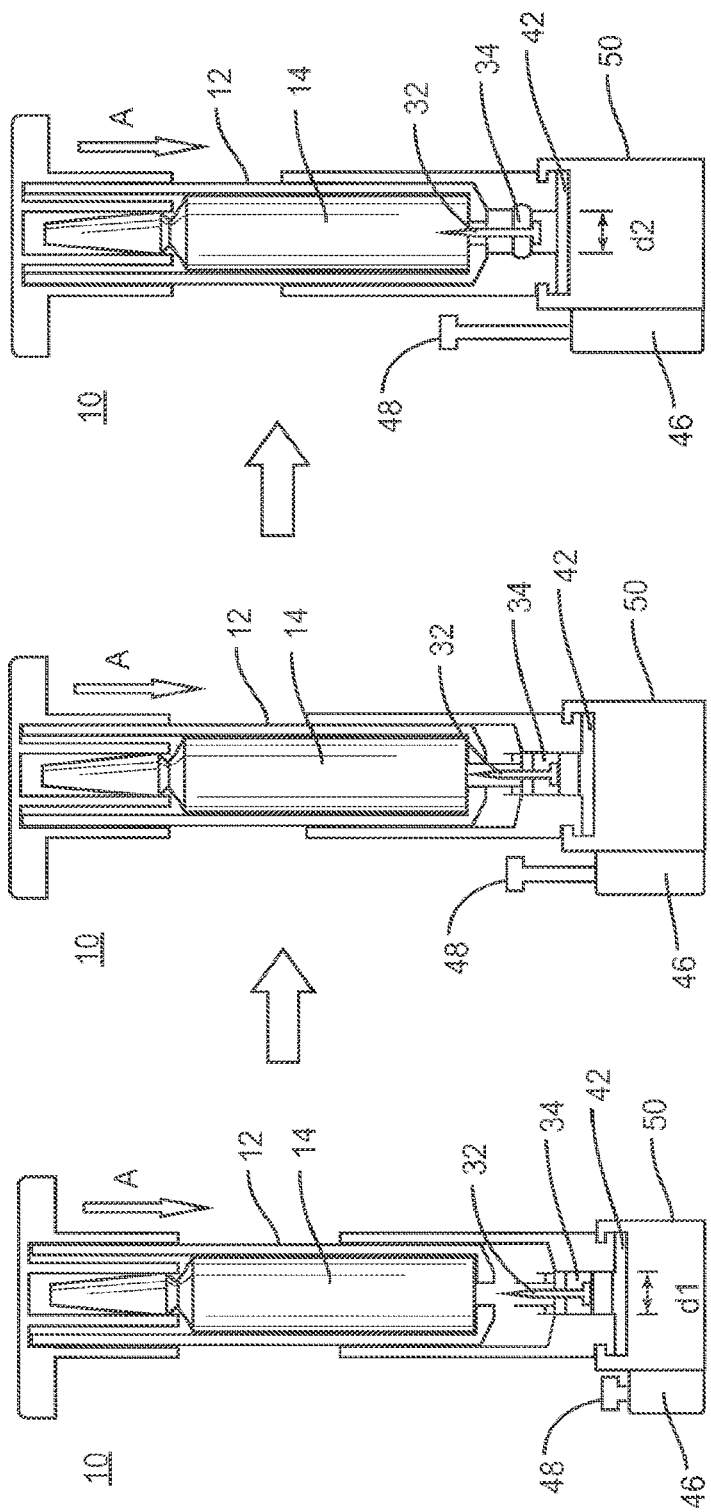

BONE CEMENT MIXING AND DELIVERY SYSTEM WITH REDUCED FUME EXPOSURE

CROSS REFERENCE TO RELATED APPLICATIONS

This application is a continuation of U.S. patent application Ser. No. 13/735,608, filed on Jan. 7, 2013, which is expressly incorporated herein by reference, in its entirety.

TECHNICAL FIELD

The present disclosure generally relates to medical devices for bone repair, and more particularly to a component injection and mixing system and method for containing fumes within a device during bone cement preparation.

BACKGROUND

Many medical procedures employ medical grade cement in connection with the restoration and strengthening of bone structures. During such procedures, cement is typically dispensed to a bone to fill in voids or spaces in the bone or between medical devices or implants attached to or embedded within the bone. These dispensing devices may include systems as simple as syringes and as complex as electronically controlled valves.

Mixing bone cement, such as, e.g., High-Viscosity Radiopaque (HV-R) bone cement, requires integration of two materials, a monomer solution, for example, a liquid that is packaged in a glass vial and a powder. One difficulty with the cement monomer is that it generates toxic fumes that ideally need to be contained to prevent inhalation exposure by medical staff. Current cement mixing techniques involve breaking the monomer vial and pouring the fluid into the powder by hand, then sealing a mixing chamber. This results in ambient exposure to fumes from the monomer component. This disclosure describes improvements over these prior art technologies.

Accordingly, an injection device, system and method for mixing bone cement and prevent the escape of toxic fumes. In one embodiment, in accordance with the principles of the present disclosure, a device for mixing and containing fumes for a bone cement component is provided that comprises a vial holder configured for receiving and holding a vial therein; a holder chamber configured to receive and secure the vial holder therein when engaged with the vial holder, the vial holder and the holder chamber forming an enclosure for containing the vial; a vial-breaking device disposed in the holder chamber, the vial holder being configured to be advanced toward the vial-breaking device for breaking the vial and for releasing contents of the vial into the holder chamber; a filter disposed within the holder chamber; and an elastomeric seal positioned about the vial-breaking device having a first surface and an opposite second surface, the first surface positioned so as to contact a surface of the vial holder and the second surface positioned to contact a surface of the holder chamber whereby advancement of the vial holder deforms the elastomeric seal from a first diameter that is smaller than the diameter of the holder chamber to a second diameter that is larger than the first diameter and forms a seal against an inside wall of the holder chamber so as to seal the upper assembly for use when dispensing cement. That is, once the vial is broken, the fluid passes by the seal, and as the user continues to turn the knob the seal expands and seals the top chamber from the lower chamber.

In one embodiment, the entire device is sealed as shipped and is only opened once the device is collapsed enough to cause the valve 48 to open. In addition, the seal also prevents fumes from escaping form the holder chamber.

The vial holder is configured to be advanced toward the vial-breaking device for breaking the vial and for releasing contents of the vial into the holder chamber. Once advanced against the elastomeric seal, the seal is compressed against a lower portion of the holder chamber to deform the seal and create a seal against the inner surface of the holder chamber. In one embodiment a filter is disposed within the holder chamber. In another embodiment, a port is in communication with the holder chamber through the filter such that when a vacuum is drawn at the port by a dispensing device, the contents of the vial can be drawn through the filter and into the dispensing device such that fumes are contained in the enclosure and the dispensing device.

In one embodiment, the system comprises a vial holder configured for receiving a vial therein and including a holding structure for maintaining the vial in the vial holder. The vial holder has an opening to expose a surface of a vial. The vial includes a monomer component for bone cement. A holder chamber is configured to receive and secure the vial holder. The vial holder is threadedly received in the holder chamber and is advanced in an advance direction by employing the threads or by being pushed in the advancing direction. The vial holder and the holder chamber form an enclosure for containing the vial. A vial-breaking device is disposed in the holder chamber. The vial holder is configured to be advanced toward the vial-breaking device for engaging the surface of the vial, breaking the vial and releasing contents, for example liquid monomer solutions, of the vial into the holder chamber past the nondeformed elastomeric seal. Once the vial holder is advanced further, the elastomeric seal is deformed to seal off the top chamber from the lower chamber and prevent fumes produced from the mixture of the monomer component with the powdered cement material from escaping from the device. In one embodiment, a filter is disposed within the holder chamber and a port in communication with the holder chamber. In this embodiment, mixed cement material can be drawn out of the holder chamber through the filter. In another embodiment, a one-way valve is disposed between the holder chamber and the port to prevent back flow into the holder chamber. A dispensing device is connectable to the port for drawing a vacuum at the port to draw the contents of the vial through the filter and into the dispensing device whereby fumes are contained in the enclosure and the dispensing device.

In one embodiment a system for containing fumes that are characteristic of the monomer itself as well as any fumes produced from the mixing of a bone cement component is provided. The system includes a vial holder configured for receiving a vial therein. A holding structure is provided for maintaining the vial in the vial holder. The vial holder has an opening to expose a surface of a vial. The vial includes a monomer component for bone cement. A holder chamber is configured to receive and secure the vial holder. The vial holder being threadedly received in the holder chamber and advanced in an advance direction by employing threads. In the alternative, a pressure fit advancement system can replace the threaded system. The vial holder and the holder chamber form an enclosure for containing the vial. A vial-breaking device is disposed in the holder chamber. The vial holder is configured to advance towards the vial-breaking device for engaging the surface of the vial, breaking the vial and releasing contents, for example, liquid monomer solutions, of the vial into the holder chamber. An elastomeric seal is positioned about the vial-breaking device. The elastomeric seal includes a first surface and an opposite second surface. The first surface of the elastomeric seal is positioned so as to contact a surface of the vial holder and the second surface of the elastomeric seal positioned to contact a surface of the holder chamber so that advancement of the vial holder compresses the elastomeric seal against the surface of the vial holder and changes the diameter of the elastomeric seal from a first diameter that is smaller than the diameter of the holder chamber to a second diameter that is larger than the first diameter. The deformed seal forms a seal against an inside wall of the holder chamber and prevents fumes from escaping from the holder chamber. A filter can be disposed within the holder chamber to retain the fumes within the chamber when the cement is being disposed. In one embodiment, a port is disposed in communication with the holder chamber through the filter. One-way valve is disposed between the holder chamber and a port to prevent back flow into the holder chamber. A dispensing device is connectable to the port for drawing a vacuum at the port so as to draw the contents of the vial through the filter and into the dispensing device such that the top chamber is isolated from the lower chamber and any fumes are contained in the enclosure.

In yet another embodiment, a method for mixing bone cement and containing fumes of the bone cement within the mixing device is provided. The method provides one of the devices or systems for containing fumes for a bone cement component of the present disclosure. The device or system includes a vial holder configured for receiving and holding a vial therein. A holder chamber configured to receive and secure the vial holder therein such that when engaged with the vial holder. The vial holder and the holder chamber form an enclosure for containing the vial. A vial-breaking device is disposed in the holder chamber. The vial holder is configured to advance toward the vial-breaking device for breaking the vial and for releasing contents of the vial into the holder chamber. An elastomeric seal and a filter are disposed within the holder chamber. A port is in communication with the holder chamber through the filter. Providing a vial containing a monomer component to react with the bone cement powder in the vial holder. Advancing the vial holder in the holder chamber breaks the vial against the vial-breaking device and releases the monomer to mix with the powder cement material. Further advancing the vial holder contacts the elastomeric seal and deforms the seal to form a seal against the inside surface of the holder chamber. This seal not only prevents the escape of toxic fumes from the enclosure and separates the top chamber from the lower chamber but also aids in compressing cement where a high-pressure seal is required for mixing and delivery of the viscous resulting cement material. Drawing a vacuum at the port by a dispensing device, for example, a syringe draws the contents of the holder chamber through the filter and into the dispensing device such that fumes are contained in the enclosure and the dispensing device.

BRIEF DESCRIPTION OF THE DRAWINGS

The present disclosure will become more readily apparent from the specific description accompanied by the following drawings, in which:

FIGS. 3A-3C are perspective views of components of the system shown in FIG. 1 in use for breaking a vial, releasing monomer to mix with powder cement, drawing its contents through a filter and loading the contents into a syringe with minimal exposure to fumes in accordance with the principles of the present disclosure.

Like reference numerals indicate similar parts throughout the figures.

DETAILED DESCRIPTION

Figure 1:
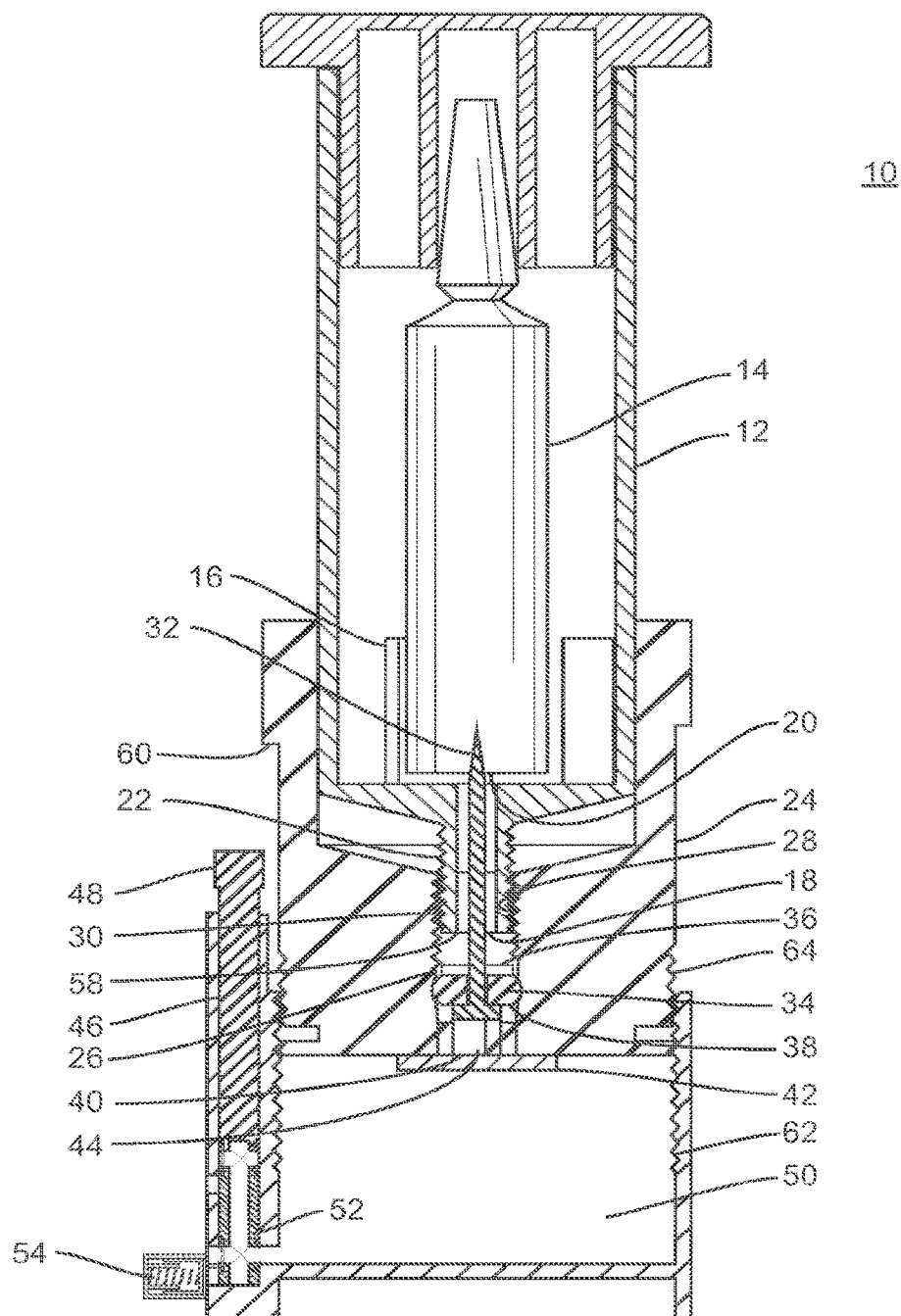
FIG. 1 is a partial cross-sectional view, with part in phantom, showing a system for mixing and containing fumes of bone cement in accordance with the principles of the present disclosure.

The exemplary embodiments of an injection system for mixing bone cement and related methods of use are disclosed in terms of medical devices for the treatment skeletal disorders and more particularly, in terms of a medical system and method for mixing bone cement while limiting exposure to fumes. It is envisioned that the medical system and method may be employed in applications such as bone treatment and repair surgeries. For example, the medical system and method can include new mixing chamber configurations.

In particularly useful embodiments, injection and mixing devices are provided that allow for breaking a monomer vial in an enclosed space to prevent fume exposure, and allowing the monomer to drip into a sealed mixing chamber passing elastomeric seal into a holder chamber having the powdered cement to mix with the monomer. These embodiments utilize a threaded chamber, which advances the monomer vial onto a vial-breaking device, e.g., a metal spike, wedges or needle. This spike causes the vial to break, permitting fluid to seep out of the vial and drip pass the elastomeric seal. As the vial holder is further advanced, the elastomeric seal is deformed and forms a seal against the inside surface of the holder chamber so as to seal off the upper chamber from the lower chamber and prevent fumes from escaping from the device. Prior to dispensing the cement the cement must be thoroughly mixed. With the aid of the seal pressure is created in the mixing chamber forcing the monomer into the powder. In alternative embodiments of the device a paddle or other agitation device, such as a metal mixing ball, can be used so as to achieve thorough mixing of the cement. Once thoroughly mixed, a connected syringe having a plunger is connected and its plunger is drawn so as to pull the contents through a filter into the syringe. The filter is designed to prevent any glass shards from passing there through. To prevent cement/monomer from flowing back into the vial chamber, a one-way valve is utilized and permits flow into the syringe but not up into the chamber.

The present embodiments may be employed in conjunction with known cement mixers (e.g., Kyphon™ cement mixers) to introduce monomer into powder in a controlled fashion. Hospitals, in particular European hospitals, are becoming increasingly sensitive to fume exposure during mixing of cements. Use of the monomer introduction devices in accordance with the present principles reduce or prevent fume exposure.

It is contemplated that one or all of the components of the medical system may be disposable, peel-pack, pre-packed sterile devices. One or all of the components of the medical system may be reusable. The surgical system may be configured as a kit with multiple sized and configured components.

It is envisioned that the present disclosure may be employed to treat or repair bone injuries or disorders such as, for example, osteoporosis, joint replacement, fracture repairs, bone breaks, etc. It is contemplated that the present disclosure may be employed with other osteal and bone related applications, including those associated with diagnostics and therapeutics. It is further contemplated that the disclosed medical systems and methods may be alternatively employed in a surgical treatment with a patient in a prone or supine position, and/or employs various surgical approaches, including anterior, posterior, posterior mid-line, direct lateral, postero-lateral, antero-lateral approaches, etc. in any body region. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a mixing system and related methods of employing the system in accordance with the principles of the present disclosure. Alternate embodiments are also disclosed. Reference will now be made in detail to the exemplary embodiments of the present disclosure, which are illustrated in the accompanying figures. Turning now to FIGS. 1-30, there are illustrated components of a medical system, such as, for example, a component extraction system 10 for use with bone cement in accordance with the principles of the present disclosure.

The components of system 10 can be fabricated from biologically acceptable materials suitable for medical applications, including metals, synthetic polymers, ceramics, glass and bone material and/or their composites, depending on the particular application and/or preference of a medical practitioner. For example, the components of system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of system 10 may have material composites, including the above materials, to achieve various desired characteristics such as strength, rigidity, elasticity, compliance, biomechanical performance, durability and radiolucency or imaging preference. The components of system 10, individually or collectively, may also be fabricated from a heterogeneous material such as a combination of two or more of the above-described materials. The components of system 10 may be monolithically formed, integrally connected or include fastening elements and/or instruments, as described herein.

System 10 is employed, for example, with an open, mini-open or minimally invasive surgical technique to fill voids, provide patches, attach prosthetic devices, etc., or any other bone related repairs or treatments.

Figure 2:
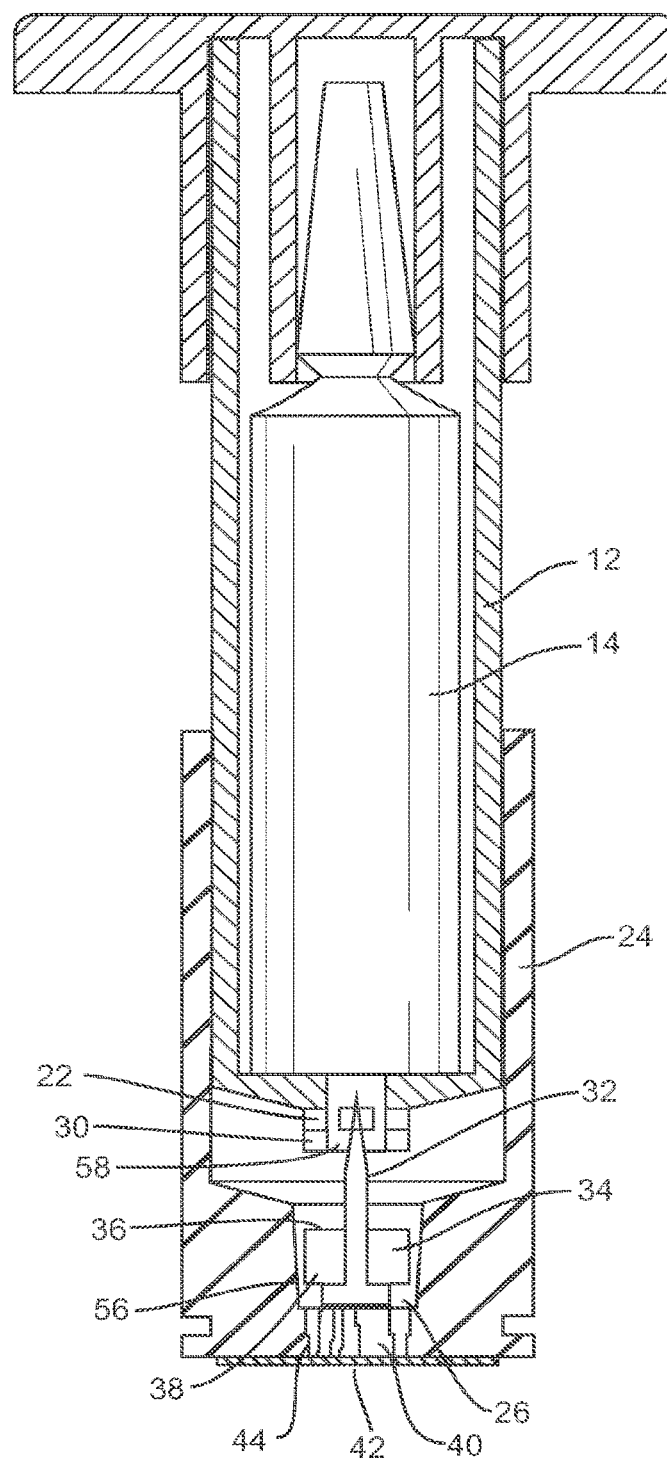
FIG. 2 is a partial cross-sectional view of the upper assembly of the mixing system shown in FIG. 1.

Referring to FIGS. 1-2, a system 10 for containing fumes for a bone cement component. System 10 includes a vial holder 12 configured for receiving a vial 14 therein. Vial 14 contains a liquid monomer component for bone cement. Vial holder 12 includes a holding structure 16 for maintaining vial 14 in vial holder 12. Vial holder 12 includes an opening 18 to expose a surface 20 of vial 14. It is contemplated that surface 20 is a thin seal such that it can be easily punctured to release the contents of vial 14. Vial holder 12 includes an engagement portion, such as, for example, a threaded portion 22 for engagement with a holder chamber 24, discussed herein. In an alternative embodiment, the engagement portion of vial holder 12 includes a threaded portion (not shown) on the exterior of the vial holder, which engages with an interior wall of the holder chamber 24. Holding structure 16 may include elastic pieces or other structures, which are configured to pinch, squeeze or otherwise hold a vial therebetween.

A holder chamber 24 is provided and includes a surface 26. Surface 26 defines an inside wall 28. Surface 26 defines an engagement portion, such as, for example a threaded portion 30. Threaded portion 30 is configured to receive and secure vial holder 12. Threaded portion 30 engages threaded portion 22 to secure vial holder 12 with holder chamber 24. This engagement forms an enclosure for containing vial 14.

A vial-breaking device, such as, for example, a spike 32 is disposed in holder chamber 24. Vial holder 12 is configured to be advanced towards spike 32 to break surface 20 of vial 14 to release the contents into the holder chamber 24 as the vial holder 12 is cranked downward. In one embodiment, the vial-breaking device may be solid and permit fluid to flow over it. In the alternative embodiment, the vial-breaking device can be configured with channels or grooves to direct the liquid monomer into the cement powder. In another alternative embodiment, the vial-breaking device is securely attached to the holding chamber 24 and can include a threaded exterior that engages with the threaded portion 22 of vial holder 12 which allows for the vial holder 12 to move downward when it is cranked relative to the vial-breaking device. In this particular embodiment the threaded vial-breaking device would need to include a passageway, for example a channel, therethrough to permit the contents of the vial 14 to pass through to the holding chamber 24 after the vial 14 is shattered by the vial-breaking device.

An elastomeric seal 34 is positioned about spike 32. Elastomeric seal 34 includes a first surface 36 and an opposite second surface 38. First surface 36 of elastomeric seal 34 is positioned so as to contact surface 58 of vial holder 12. Second surface 38 of elastomeric seal 34 is positioned so as to contact surface 26 of holder chamber 24. As vial holder 12 is advanced towards spike 32, elastomeric seal 34 is compressed against surface 58 of vial holder 12 so as to change the diameter of elastomeric seal from a first diameter $d_1$ that is smaller than the diameter of holder chamber 24 to a second diameter $d_2$ that is larger than first diameter $d_1$ to form a seal against inside wall 28 of holder chamber 24. This seal prevents fumes from escaping from holder chamber 24.

A port 40 is disposed in communication with holder chamber 24 through a filter 42. Filter 42 is disposed within holder chamber 24 which can be positioned above or below the seal. Filter 42 may include a porous solid, a fabric or mesh configured to trap particles, or foreign material including glass or fragments from the breakage of the vial. A one-way valve 44 is provided to receive filtered material. One-way valve 44 ensures that liquid moving therethrough is not permitted to flow back and reenter the holder chamber 24. In one embodiment, port 40 includes a luer-lock fitting. Port 40 is connected to the holder chamber 24 by a lumen 56. Lumen 56 is disposed in line with the advancing direction of vial holder 12.

A dispensing device, such as, for example, a syringe 46 is connected to port 40 for drawing a vacuum at port 40 to draw the contents of vial 14 through filter 42 and into syringe 46 such that fumes are contained in the enclosure and the dispensing device. Syringe 46 includes a plunger 48. Syringe 46 provides a sealed connection with port 40 and a vacuum by pulling plunger 48. Syringe 48 is connected to port 40 such that syringe 46 is parallel to an advancing direction of vial holder 12. In one embodiment, syringe 46 is docked with port 40 such that syringe 46 is disposed transverse to the advancing direction of vial holder 12.

A mixing chamber 50 includes a wall 52 and a port 54. Port 54 is configured to receive syringe 46 to permit dispensing of the contents of syringe 46 through wall 52 of the mixing chamber such that fumes are contained in mixing chamber 50 and syringe 46. Mixing chamber 50 contains a powder component of bone cement for mixing with the liquid monomer in the vial. In one embodiment, port 54 includes a luer lock. In one embodiment port 54 includes a sealable membrane configured to be penetrated by syringe 46. In one particular embodiment, the mixing chamber 50 has a threaded portion 62 that is engaged to a threaded portion 64 of holding chamber 24 allowing the holding chamber 24 to be moved downward by continuing to crank the vial holder 12 after the elastomeric seal 34 has sealed the holding chamber 24 from the mixing chamber 50.

Referring to FIGS. 3A-3C, a method for employing the device 10 of FIG. 1 is illustratively shown in accordance with one embodiment. FIG. 3A includes a vial 14 inside the vial holder 12. The vial holder 12 supports the vial 14 and provides a spacing to enable proper operation of the device 10. The vial holder 12 encloses the vial 14. The vial holder 12 includes threads 22 or other connection mechanism to engage threads 30 of the holder chamber 24. A syringe 46 is attached to mixing chamber 50. In the alternative, a chamber having a punctuable membrane is attached to mixing chamber 50. The punctuable membrane is configured so that syringe 46 can be inserted therein so as to draw the mixed cement into the syringe for deployment. Plunger 48 of the syringe is shown in a fully advanced (closed) position.

In FIG. 3B, the vial 14 is advanced as shown by arrow A in FIG. 3B by screwing down the vial holder 12 using, e.g., handle 2. In another embodiment, vial holder 12 is advanced by exerting a downward force, thus acting as a syringe-plunger mechanism. As the vial 12 is advanced, the vial 14 is broken when it comes in contact with the spike 32 disposed in holder chamber 12. The broken vial 14 permits the fluid to flow around spike 32, around the elastomeric filter and through to the filter 42 and into mixing chamber 50. As vial 14 is advanced, either by being cranked or pushed down, elastomeric seal 34 is compressed from an initial diameter $d_1$ to a final diameter $d_2$, as shown in FIGS. 3A and 3C. The expanded diameter of the elastomeric seal 34 closes (seals) the mixing chamber 50 preventing migration of mixed cement into the vial chamber and prevents fumes from escaping from the device. The contents of the vial may flow through one-way valve 44 provided to receive filtered material. The one-way valve 44 ensures that liquid moving therethrough is not permitted to flow back.

In FIG. 3C, the plunger 48 is extended (opened) to allow contents of the mixing chamber 50, through the one-way valve 44 into the syringe chamber. That is, depressing and rotating automatically engages ledge 60 of holding chamber 24 with plunger 48. In this configuration, cement is forced out of the mixing chamber 50 by screwing the vial holder 12 or the holding chamber 24 which causes the holding chamber 24, which in this particular embodiment is threadedly attached to the mixing chamber 50, to move downward forcing the contents of the mixing chamber into the syringe 46. The contents can then be pushed out of the port 54 either by continuing to rotate the holding chamber 50 or the vial holder 12 or by pushing on the plunger 48 of the syringe 46. The continuing cranking of the vial holder causes the ledge 60 of the holding chamber 24 to engage with the plunger 48 pushing the plunger 48 down which opens the stop cock/port 54 driving the contents out of the syringe 46. Suction created by the syringe could also be used; however since the cement is very viscous it is unlikely that vacuum created by the syringe alone would be sufficient to draw up the cement from the mixing chamber 50 and push the cement out of the syringe 46. The mixed bone cement is contained at all times within the mixing chamber 50 and/or the syringe. Since the entire procedure maintains the contents of the mixing chamber 50 within the enclosure formed by the elastomeric seal 34 and components of the system 10, fumes from the contents of the mixing chamber 50 are reduced, minimized or eliminated.

In this example, the bone cement may be formed from a powder (e.g., pre-polymerized PMMA and/or PMMA or MMA co-polymer beads and/or amorphous powder, radio-opaque, initiator) and the liquid (e.g., MMA monomer, stabilizer, and inhibitor). The two components are mixed, and a free radical polymerization occurs when the components are mixed. The bone cement viscosity changes over time from a runny liquid into a dough-like material that can be applied and then finally hardens into solid hardened material. The mixture is mixed or infused by a mixing element.

In assembly, operation and use, system 10 described above, are employed in a surgical procedure, such as, for the treatment or repair of bones. For example, as shown in FIGS. 1-3C, system 10 can be employed for safer mixing of bone cement components for the treatment and repair of bones, to strengthen or rebuild bones, etc. It is contemplated that one or all of the components of system 10 can be delivered or employed as a pre-assembled device or can be assembled in situ. System 10 may be completely or partially revised, removed or replaced. In one embodiment, the holder chamber 24 (and/or vial holder 12) may be shipped having vials 14 contained therein. In other words, a packed kit may include system 10 including a vial 14 contained in a vial holder 12 with holder chamber 24 and an optional syringe 46 with a compatible fitting.

For example, as shown in FIGS. 1-30, system 10, described above, can be employed during a surgical procedure for mixing and dispensing bone cement. In use, a medical practitioner obtains access to a surgical site including a bone in any appropriate manner, such as through incision and retraction of tissues. It is envisioned that system 10 can be used in any existing surgical method or technique including open surgery, mini-open surgery, minimally invasive surgery and percutaneous surgical implantation, whereby the bone is accessed through a mini-incision, or sleeve that provides a protected passageway to the area. Once access to the surgical site is obtained, the particular surgical procedure can be performed for treating or repairing the bone.

An incision is made in the body of a patient and a cutting instrument (not shown) creates a surgical pathway for implantation of components for supplying bone cement mixed using system 10. A preparation instrument (not shown) can be employed to prepare tissue surfaces of the bone, as well as for aspiration and irrigation of a surgical region according to the requirements of a particular surgical application.

Holes, fractures, voids, depressions, etc. may exist in the bone or may be created in the bone as part of the procedure. After appropriate steps are taken for the treatment or repair, these holes, fractures, voids, depressions, etc. are filled with the mixed bone cement to maintain or improve the bone's structural integrity. Components are delivered to the surgical site along the surgical pathway(s) and into or onto bone tissue.

In one embodiment, an agent may be mixed with or delivered with bone cement (in, e.g., in the two components) or delivered separately. It is envisioned that the agent may include bone growth promoting material.

It is contemplated that the agent may include therapeutic polynucleotides or polypeptides. It is further contemplated that the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. Components can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

It is envisioned that the use of microsurgical and image guided technologies may be employed to access, view and repair bone deterioration or damage. Upon completion of the procedure, the surgical instruments and assemblies are removed and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A mixing device comprising:
   a vial holder;
   a container configured to receive and secure the vial holder therein when engaged with the vial holder, the vial holder and the container forming an enclosure for containing a vial, the container comprising a ledge and a vial-breaking device; and
   a mixing vessel comprising a mixing chamber, the vial holder being configured to be advanced toward the vial-breaking device to break the vial and for releasing contents of the vial such that the contents move into the mixing vessel,
   the mixing vessel comprising a port and a syringe that is in communication with the port, the syringe comprising a plunger that is movable within the syringe to draw the contents into the syringe, the mixing vessel being movable relative to the container between a first orientation in which the ledge is spaced apart from the plunger and a second orientation in which the ledge engages the plunger to move the plunger relative to the syringe and drive the contents out of the syringe and the port, wherein the vial holder comprises a threaded outer surface and the container comprises a threaded inner surface configured to engage the threaded outer surface to move the vial holder axially relative to the container, and wherein the mixing vessel comprises a threaded inner surface that engages a threaded outer surface of the container to move the container axially relative to the mixing vessel.

2. The mixing device recited in claim 1, wherein the container comprises an elastomeric seal having a first surface and an opposite second surface, the seal being positioned such that the vial-breaking device extends through the first and second surfaces.

3. The mixing device recited in claim 2, wherein the seal is configured to form a seal against an inner surface of the container so as to prevent fumes from escaping from the container.

4. The mixing device recited in claim 3, wherein the seal forms a seal against an unthreaded inner surface when the container is in the second orientation so as to prevent fumes from escaping from the container.

5. The mixing device recited in claim 1, further comprising the vial.

6. The mixing device recited in claim 5, wherein the vial-breaking device is a spike that extends into the vial when the container is in the second orientation.

7. The mixing device recited in claim 5, wherein the vial-breaking device comprises a passageway that extends through the vial-breaking device to allow contents of the vial to pass through the container and into the mixing vessel.

8. A mixing device comprising:
a vial holder;
a vial coupled to the vial holder;
a container configured to receive and secure the vial holder therein when engaged with the vial holder, the vial holder and the container forming an enclosure for containing the vial, the container comprising a ledge and a vial-breaking device, the container comprising an elastomeric seal positioned such that the vial-breaking device extends through the seal;
a mixing vessel comprising a mixing chamber, the vial holder being configured to be advanced toward the vial-breaking device to break the vial and for releasing contents of the vial such that the contents move into the mixing vessel,
the mixing vessel comprising a port and a syringe that is in communication with the port, the syringe comprising a plunger that is movable within the syringe to draw the contents into the syringe, the mixing vessel being movable relative to the container between a first orientation in which the ledge is spaced apart from the plunger and a second orientation in which the ledge engages the plunger to move the plunger relative to the syringe and drive the contents out of the syringe and the port; and
a one-way valve disposed between the enclosure and the mixing chamber to prevent back flow into the enclosure,
wherein the vial holder comprises a threaded outer surface and the container comprises a threaded inner surface configured to engage the threaded outer surface to move the vial holder axially relative to the container, and wherein the mixing vessel comprises a threaded inner surface that engages a threaded outer surface of the container to move the container axially relative to the mixing vessel.

9. A mixing device comprising:
a vial holder;
a container, the vial holder and the container forming an enclosure, the container comprising a vial-breaking device; and
a mixing vessel comprising a mixing chamber, a port, a syringe that is in communication with the port and a plunger that is movable within the syringe,
wherein the vial holder comprises a threaded outer surface and the container comprises a threaded inner surface configured to engage the threaded outer surface to move the vial holder axially relative to the container, and
wherein the mixing vessel comprises a threaded inner surface that engages a threaded outer surface of the container to move the container axially relative to the mixing vessel, and
wherein the enclosure is configured for disposal of a vial, the vial-breaking device being configured to break the vial to release contents of the vial into the mixing vessel when the vial holder is advanced toward the vial-breaking device, the plunger being movable to draw the contents into the syringe, the contents being driven out of the syringe and the port when the mixing vessel is in the second orientation.

10. The mixing device recited in claim 9, wherein the container includes a ledge, the mixing vessel being movable relative to the container between a first orientation in which the ledge is spaced apart from the plunger and a second orientation in which the ledge engages the plunger to move the plunger relative to the syringe.

11. The mixing device recited in claim 9, wherein the container comprises an elastomeric seal having a first surface and an opposite second surface, the seal being positioned such that the vial-breaking device extends through the first and second surfaces.

12. The mixing device recited in claim 11, wherein the seal is configured to form a seal against the container so as to prevent fumes from escaping from the container.

13. The mixing device recited in claim 11, wherein the seal forms a seal against an unthreaded inner surface of the container so as to prevent fumes from escaping from the container.

14. The mixing device recited in claim 9, wherein the vial-breaking device is a spike.

15. The mixing device recited in claim 9, wherein the vial-breaking device comprises a passageway that extends through the vial-breaking device to allow a liquid to pass through the container and into the mixing vessel.

16. The mixing device recited in claim 9, further comprising the vial.

17. The mixing device recited in claim 16, wherein the vial-breaking device is a spike that extends into the vial when the container is in the second orientation.

18. The mixing device recited in claim 16, wherein the vial-breaking device comprises a passageway that extends through the vial-breaking device to allow contents of the vial to pass through the container and into the mixing vessel.

19. The mixing device recited in claim 9, further comprising a one-way valve disposed between the enclosure and the mixing chamber to prevent back flow into the enclosure.

* * * * *